United States Patent
Midorikawa et al.

(10) Patent No.: US 8,546,634 B2
(45) Date of Patent: Oct. 1, 2013

(54) METHOD FOR PRODUCTION OF CONJUGATED DIOLEFIN

(75) Inventors: Hideo Midorikawa, Tokyo (JP); Hiroyuki Yano, Tokyo (JP); Takashi Kinoshita, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 180 days.

(21) Appl. No.: 12/893,339

(22) Filed: Sep. 29, 2010

(65) Prior Publication Data
US 2012/0078026 A1 Mar. 29, 2012

(51) Int. Cl.
*C07C 5/09* (2006.01)
*C07C 5/327* (2006.01)

(52) U.S. Cl.
USPC .......... 585/631; 585/621; 585/627; 585/629; 585/630; 502/304; 502/302; 502/306; 502/311; 502/315; 502/316; 502/319; 502/321; 502/322; 502/323; 502/324; 502/326; 502/329; 502/335; 502/336; 502/337; 502/338; 502/341; 502/342; 502/343; 502/354; 502/355

(58) Field of Classification Search
None
See application file for complete search history.

(56) References Cited

U.S. PATENT DOCUMENTS

| | | | | |
|---|---|---|---|---|
| 3,709,951 A | * | 1/1973 | Hutson, Jr. et al. | ........... 585/501 |
| 4,388,223 A | | 6/1983 | Ferlazzo et al. | |
| 4,547,615 A | * | 10/1985 | Yamamoto | .................... 585/621 |
| 4,595,788 A | | 6/1986 | Yamamoto et al. | |

FOREIGN PATENT DOCUMENTS

| | | |
|---|---|---|
| JP | 45-17407 | 6/1970 |
| JP | 49-14392 | 4/1974 |
| JP | 60-126235 | 7/1985 |
| JP | 61-12488 | 4/1986 |
| JP | 3-16929 | 3/1991 |
| JP | 3-48891 | 7/1991 |
| JP | 2010-120933 | 6/2010 |

OTHER PUBLICATIONS

Masayuki Horio et al., Fluidized Bed Handbook, Baifukan, 1999, pp. 6-13.
Sekiyu Gakkai et al., Petrotech, 1978, vol. 2, No. 4, pp. 59-65.

* cited by examiner

*Primary Examiner* — In Suk Bullock
*Assistant Examiner* — Jelitza Perez
(74) *Attorney, Agent, or Firm* — Finnegan, Henderson, Farabow, Garrett & Dunner, L.L.P.

(57) ABSTRACT

There is provided a method for production of a conjugated diene from a monoolefin having four or more carbon atoms by a fluidized bed reaction. The method for production of a conjugated diolefin includes bringing a catalyst in which an oxide is supported on a carrier into contact with a monoolefin having four or more carbon atoms in a fluidized bed reactor in which the catalyst and oxygen are present, wherein the method satisfies the following (1) to (3):
  (1) the catalyst contains Mo, Bi, and Fe;
  (2) a reaction temperature is in the range of 300 to 420° C.; and
  (3) an oxygen concentration in a reactor outlet gas is in the range of 0.05 to 3.0% by volume.

8 Claims, No Drawings

METHOD FOR PRODUCTION OF CONJUGATED DIOLEFIN

BACKGROUND

1) Field of the Invention

The present invention relates to a method for production of a conjugated diolefin by a fluidized bed reaction system using an oxide catalyst.

2) Description of Related Art

A method for subjecting monoolefins having four or more carbon atoms such as n-butene and isopentene and molecular oxygen to catalytic oxidative dehydrogenation to produce conjugated diolefins corresponding to these monoolefins such as 1,3-butadiene and isoprene, respectively, is well known, and many catalysts used for the oxidative dehydrogenation are proposed.

An important reaction in the chemical industry is a heterogeneous reaction in which two phases such as gas-solid are involved, and ammonia synthesis, ethylene oxide synthesis, catalytic cracking of oil, and the like are known as heterogeneous reactions in which oxide catalysts are industrially used.

A reaction system in which an oxide catalyst is used includes a fixed bed, a fluidized bed, and a moving bed. Among these, a fixed bed reaction system is frequently industrially employed utilizing the advantage that the fluid state of gas is close to an extruding flow and the reaction yield can be increased. However, the fixed bed reaction system has a low heat transfer performance and is unsuitable for an exothermic reaction and an endothermic reaction requiring cooling and heating, respectively. Particularly, in an intense exothermal reaction like oxidation reaction, there is a problem that the temperature rapidly rises to a state where it is difficult to be controlled and there is a possibility that a reaction may proceed extremely may be initiated. There is also a problem that a catalyst will suffer damage and will deteriorate at an early stage by such a rapid temperature rise.

On the other hand, the fluidized bed reaction system, in which catalyst particles are moving rapidly in the reactor, has advantages that (1) it has a high heat transfer performance, can maintain the temperature in the reactor at a substantially constant level even during a highly exothermic or endothermic reaction, and can suppress excessive reaction progress; and (2) since local accumulation of energy is suppressed, a raw material gas within the range of explosion can be reacted safely, and so it is possible to increase the raw material concentration to improve productivity. Therefore, the fluidized bed reaction system is suitable for the oxidative dehydrogenation of hydrocarbons which is a strong exothermic reaction. For example, the oxidative dehydrogenation to synthesize 1,3-butadiene from butene is an exothermic reaction of about 30 kcal/mol.

Although advantageous points of the fluidized bed reaction system as described above are known, Patent Documents 1 and 2, for example, describe that when unsaturated hydrocarbons are generally converted to unsaturated aldehydes or diolefins, the use of a fixed bed catalyst is preferred. Further, Patent Document 3 describes that in the production of conjugated dienes by the oxidative dehydrogenation of monoolefins, the catalyst described in the Patent Document can be used in all the methods of a fixed bed, a moving bed, and a fluidized bed, but there is no specific description in it about reaction systems other than a fixed bed.

[Patent Document 1] Japanese Patent Publication No. 49-14392

[Patent Document 2] Japanese Patent Publication No. 61-12488

[Patent Document 3] Japanese Patent Publication No. 03-16929

SUMMARY

The reason why a fixed bed reaction system is practically employed although it is recognized that the fluidized bed reaction system advantageous to the temperature control in a reactor is suitable for industrial practice is estimated by the present inventors as follows. Since a conjugated diolefin which is an objective product has very high reactivity, it is susceptible to oxidative decomposition in a reactor by the time it arrives at a reactor exit. Sometimes, the reactivity of a conjugated diolefin which is a product is higher than that of a monoolefin which is a raw material. A conjugated diolefin can be decomposed in an atmosphere where oxygen is present at high temperatures. In addition to the fact, the decomposition is supposed to be further promoted in a fluidized bed reaction system in which a product contacts a catalyst. As a result, the yield drop of the conjugated diolefin is unavoidable in the fluidized bed reaction system. The problem of the decomposition of a product is a problem that cannot occur in the fixed bed reaction system in which a product does not continue contacting a catalyst, and it can be said to be a problem peculiar to the fluidized bed reaction system.

Namely, the production of a conjugated diolefin by the oxidative dehydrogenation of a monoolefin by the fluidized bed reaction system which must be industrially advantageous has not been put in practical use from the viewpoint of temperature control but the fixed bed reaction system has only been used because there may be no means for preventing decomposition of the highly reactive conjugated diolefin. That is, it is conjectured that the fixed bed reaction system excellent in recovery of a product had to be employed even at the expense of industrial efficiency, in order to prevent decomposition of a product to ensure a required yield.

As a result of extensive and intensive studies for solving the above problems, the present inventors have found that when a conjugated diene is produced from a monoolefin having four of more carbon atoms by a fluidized bed reaction, the decomposition of the conjugated diolefin which is a product can be effectively suppressed even when a fluidized bed reaction system is employed, by using an oxide catalyst containing Mo, Bi, and Fe and having a carrier at a specific reaction temperature and setting the oxygen concentration in a reactor outlet gas to a specific range. The present invention has been achieved on the basis of these findings.

That is, the present invention is as follows.

[1]

A method for production of a conjugated diolefin comprising bringing a catalyst in which an oxide is supported on a carrier into contact with a monoolefin having four or more carbon atoms in a fluidized bed reactor in which the catalyst and oxygen are present, wherein the method satisfies the following (1) to (3):

(1) the oxide contains Mo, Bi, and Fe;

(2) a reaction temperature is in the range of 300 to 420° C.; and (3) an oxygen concentration in a reactor outlet gas is in the range of 0.05 to 0.7% by volume.

[2]

The method for production of the conjugated diolefin according to [1], wherein the carrier is at least one selected from the group consisting of silica, alumina, titania, and zirconia.

[3]

The method for production of the conjugated diolefin according to [1] or [2], wherein an atomic ratio of Bi of p and an atomic ratio of Fe of q to an atomic ratio of Mo of 12 in the oxide satisfy 0.1≤p≤5 and 0.5≤q≤8.

[4]

The method for production of the conjugated diolefin according to any one of [1] to [3], wherein the oxide is represented by the following empirical formula:

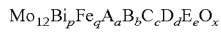

$$Mo_{12}Bi_pFe_qA_aB_bC_cD_dE_eO_x$$

wherein A is at least one element selected from the group consisting of nickel and cobalt; B is at least one element selected from alkali metal elements; C is at least one element selected from the group consisting of magnesium, calcium, strontium, barium, zinc, and manganese; D is at least one rare earth element; E is at least one element selected from the group consisting of chromium, indium, and gallium; O is oxygen; p, q, a, b, c, d, e, and x represent an atomic ratio of bismuth, iron, A, B, C, D, E, and oxygen, respectively, to 12 molybdenum atoms; 0.1≤p≤5, 0.5≤q≤8, 0≤a≤10, 0.02≤b≤2, 0≤c≤5, 0≤d≤5, and 0≤e≤5 are satisfied; and x is a number of oxygen atoms required for satisfying a valence requirement of other elements present.

[5]

The method for production of the conjugated diolefin according to any one of [1] to [4], wherein the monoolefin having four or more carbon atoms is n-butene or isopentene.

According to the present invention, a conjugated diolefin can be obtained in high yield while preventing the oxidative decomposition of the product by subjecting a monoolefin having four or more carbon atoms to catalytic oxidative dehydrogenation in a fluidized bed reactor in which oxygen and a specific catalyst are present.

DETAILED DESCRIPTION

Hereinafter, the best mode for carrying out the present invention (hereinafter referred to as the present embodiments) will be described in detail. Note that the present invention is not limited to the following embodiments but can be carried out by variously modifying them within the scope of the gist thereof.

[1] Method for Production of a Conjugated Diolefin
(1) Raw Material

The raw material is a monoolefin having four or more carbon atoms. The monoolefin is an organic compound having only one carbon-carbon double bond and does not usually have a functional group, and is a linear and/or branched chain hydrocarbon. Although the upper limit of the number of the carbon atoms is not strict, it is preferably six or less in terms of reactivity. Examples of the monoolefin having four or more carbon atoms include n-butene (1-butene and 2-butene), 1-pentene, 2-pentene, isopentene (2-methyl-1-butene and 3-methyl-1-butene), 1-hexene, 2-hexene, and 2,3-dimethyl-butene. One monoolefin may be used as a raw material, or two or more monoolefins may be used as a raw material. A monoolefin which is liquid at ordinary temperature (5 to 35° C.) is preferably subjected to reaction after it is gasified with a gasifier having a heating unit using steam, a heat transfer coil, or the like.

The monoolefin is not necessarily highly purified, and any mixture or an industrial grade can be used as the monoolefin. For example, in the case of n-butene, the following raw materials can be used: a residual component obtained by extracting 1,3-butadiene from a C4 fraction byproduced in naphtha thermal cracking; a residual component obtained by further extracting isobutylene from the residual component; a C4 fraction byproduced in fluidized catalytic cracking (FCC) for decomposing a heavy oil fraction by catalysis to convert it into a low-boiling point hydrocarbon; a butene fraction obtained by dehydrogenation or oxidative dehydrogenation of n-butane; or a C4 fraction byproduced in the catalytic conversion of ethylene obtained by ethane thermal cracking or dehydration of biomass ethanol. Biomass ethanol is ethanol obtained from biomass, and specific examples include ethanol obtained by fermentation of sugarcane, corn, and the like and ethanol obtained from woody resources such as scrap wood, thinner timber, rice straw, and agricultural products.

The monoolefin concentration in the raw material is preferably 2% by volume or more based on 100% by volume of a raw material mixed gas containing at least monoolefin and air from the viewpoint of the productivity of a conjugated diolefin, and preferably 30% by volume or less from the viewpoint of suppressing the load to a catalyst. The concentration is more preferably in the range of 3 to 25% by volume. When the concentration is high, there is a tendency of increase in the accumulation of reaction products and the deposition of a coke on the catalyst and decrease in the catalyst life due to the degradation of the catalyst. When the concentration is low, the production volume of a conjugated diolefin is small, and there is no practical advantage.

The raw material mixed gas may contain paraffins, water, steam, hydrogen, nitrogen, carbon dioxide, carbon monoxide, and the like. Examples of paraffins can include methane, ethane, propane, butane, pentane, hexane, heptane, octane, and nonane. After 1,3-butadiene which is an objective product is separated from a reaction product, it is also possible to recycle at least part of unreacted butene to a fluidized bed reactor.

(2) Reactor

The production of a conjugated diolefin by the oxidative dehydrogenation of a monoolefin having four or more carbon atoms is performed by the fluidized bed reaction system.

The fluidized bed reactor has a structure having a gas distributor, an inserted object, and a cyclone as the main components in the reactor, wherein the catalyst is fluidized to bring it into contact with a gas which is a raw material. A fluidized-bed reactor described in the Fluidized Bed Handbook (published by Baifukan, 1999) or the like can be used, and a reactor of the bubbling fluidized bed system is particularly suitable. The heat of reaction generated can be removed by using a cooling pipe inserted into the reactor.

(3) Reaction Conditions

A monoolefin and oxygen are subjected to reaction. Air is generally used as an oxygen source, and it is also possible to use a gas having an increased oxygen concentration prepared, for example by mixing oxygen with air or a gas having a decreased oxygen concentration prepared, for example by mixing an inert gas such as helium and nitrogen with air. The molar ratio of oxygen to a monoolefin in terms of the oxygen/monoolefin ratio is preferably in the range of 0.5 to 2.5, more preferably 0.6 to 2.1.

As long as the gases subjected to reaction are within the ratio as described above, a method for introducing a monoolefin and oxygen is not limited. A gas containing a monoolefin is previously mixed with air or with a gas having an increased or decreased oxygen concentration, before these gases are introduced into a reactor filled with a catalyst, or each of these gases may be independently introduced into the reactor. Although the gases subjected to reaction can be increased to a predetermined reaction temperature after they are introduced into the reactor, the gases are usually preheated before being introduced into the reactor in order to allow them to continuously and efficiently react with each other.

The reaction temperature is controlled in the range of 300 to 420° C. If the reaction temperature is less than 300° C., the conversion of a monoolefin will be low, and if it exceeds 420° C., a conjugated diolefin produced tends to be increasingly burned and decomposed. The reaction temperature is preferably in the range of 320 to 400° C., more preferably in the range of 340 to 380° C. Since the reaction for producing a conjugated diolefin is an exothermic reaction, generated heat is typically removed so that a suitable reaction temperature will be obtained. The reaction temperature can be controlled within the range as described above by removing the reaction heat with a cooling pipe or supplying heat with a heating device.

The reaction can be performed at a pressure in the range of from a slightly reduced pressure to 0.8 MPa. The contact time between a raw material mixed gas and a catalyst is in the range of 0.5 to 20 g·sec/cc, preferably in the range of 1 to 10 g·sec/cc.

Contact of the catalyst with the raw material mixed gas in the reactor produces a conjugated diolefin corresponding to the monoolefin. For example, when the monoolefin is n-butene, the main product is 1,3-butadiene, and when the monoolefin is isopentene, the main product is isoprene. The yield and/or selectivity of a product depends on a raw material, a catalyst, reaction temperature, and the like. Therefore, these materials and conditions may be suitably set in the ranges where the requirements of the present invention are satisfied depending on the objective product.

The gas containing the conjugated diolefin produced flows out of a reactor exit. Since the oxygen concentration in the reactor outlet gas influences the decomposition and the side reaction of the objective product in the reactor, control of the concentration within a suitable range is important. The oxygen concentration in the reactor outlet gas can be controlled by changing the amount of a gas used as the oxygen source to be supplied to the reactor, for example, the amount of air to be supplied to the reactor, reaction temperature, pressure in the reactor, the amount of a catalyst, and the total gas volume to be supplied to the reactor. The oxygen concentration in the reactor outlet gas is preferably controlled by changing the amount of a gas used as the oxygen source to be supplied to the reactor, for example, the amount of air. For example, when 50 g of an oxide represented by $Mo_{12}Bi_{0.60}Ce_{0.75}Fe_{1.8}Ni_{5.0}Mg_{2.0}K_{0.09}Rb_{0.05}O_x$ is used as a catalyst and a raw material gas is supplied at a flow rate of 654 cc/min (in terms of NTP) at a reaction temperature of 350° C. and a reaction pressure of 0.05 MPa, the oxygen concentration in the reactor outlet gas can be changed from 0.2% by volume to 0.5% by volume by changing the molar ratio composition of the raw material gas from 1-butene/air/helium=1/3.4/balance (1-butene concentration=12% by volume) to 1-butene/air/helium=1/3.8/balance (1-butene concentration=12% by volume). Note that "1-butene/air/helium=1/3.8/balance (1-butene concentration=12% by volume)" indicates that the amount of helium is determined so that 1-butene/air=1/3.8 and 1-butene concentration may satisfy 12% by volume.

Reduction of the catalyst in the reactor and decomposition of the objective product can be effectively prevented by maintaining the oxygen concentration in the reactor outlet gas in the range of 0.05 to 0.7% by volume based on the whole reactor outlet gas. The oxygen concentration in the reactor outlet gas is preferably in the range of 0.1 to 0.6% by volume, more preferably in the range of 0.2 to 0.5% by volume. If the oxygen concentration in the reactor outlet gas is less than 0.05% by volume, the catalyst will undergo reduction and the conversion of a monoolefin will be low. If the oxygen concentration exceeds 0.7% by volume, the production of an oxygen-containing compound by the oxidative decomposition and the side reaction of a conjugated diolefin produced tend to increase, thus reducing the yield of the conjugated diolefin. Generally, since the flow velocity of the outlet gas is large enough, the measured value will not be influenced by the position of a line for sampling, even when the line is provided by branching in the downstream of the outlet or it is provided near the outlet. The oxygen concentration in the reactor outlet gas can be measured by gas chromatography provided with a thermal conductivity detector (TCD).

(4) Purification

The reaction product obtained in the fluidized bed reaction can be purified by a known technique, for example by a method described in Japanese Patent Publication No. 45-17407, Japanese Patent Application Laid-Open No. 60-126235, Japanese Patent Publication No. 03-48891, or PETROTECH, vol. 2, No. 4, pp. 59-65, 1978. When the conjugated diolefin concentration in the reaction product after purification is 99% or more, the purified product can be suitably used as a high purity conjugated diolefin, as a raw material for a synthetic rubber and the like.

[2] Catalyst (1) Structure

The catalyst in which an oxide is supported on a carrier contains a carrier, Mo, Bi, and Fe. The composition of Mo, Bi, and Fe is adjusted so as to form an appropriate oxide, and the oxidative dehydrogenation from a monoolefin to a conjugated diolefin is probably performed by the lattice oxygen in this oxide. Generally, when the lattice oxygen in the catalyst is consumed in the oxidative dehydrogenation, oxygen holes will be produced in the oxide. As a result, the reduction of the oxide also advances with the progress of the reaction to deactivate the catalyst. Therefore, it is necessary to quickly reoxidize the oxide which has undergone reduction in order to maintain the catalytic activity. The oxide containing Mo, Bi, and Fe is excellent not only in the reactivity in the oxidative dehydrogenation from a monoolefin to a conjugated diolefin but also probably in the reoxidation function of dissociatively adsorbing molecular oxygen in the gaseous phase to take it into the oxide to regenerate the consumed lattice oxygen. Therefore, the reoxidation function by regenerating the lattice oxygen is probably maintained even when the reaction is carried out over a long period of time, and the catalyst can stably produce a conjugated diolefin from a monoolefin without being deactivated.

The use of a catalyst in which an oxide containing Mo, Bi, and Fe is supported on a carrier for production of a conjugated diolefin by a fluidized bed system is advantageous to suppress the formation of an oxygen-containing compound by the oxidative decomposition and the side reaction of the conjugated diolefin which is a product, and the conjugated diolefin can be obtained in high yield. Details are not known, but the following reasons are considered: (1) since the acidity of the catalyst is suitable, the oxidative decomposition and the side reaction of a conjugated diolefin on the catalyst are low; and (2) since the adsorption ability of an active site to the produced conjugated diolefin is low, the conjugated diolefin is probably desorbed quickly after it is produced and before it undergoes decomposition and reaction at the active site.

Since Mo, Bi, and Fe easily form an appropriate oxide, the composition ratio of these atoms is probably as follows: an atomic ratio of Bi of p and an atomic ratio of Fe of q to an atomic ratio of Mo of 12 in the oxide satisfy $0.1 \leq p \leq 5$ and $0.5 \leq q \leq 8$.

When the oxide contains metals other than Mo, Bi, and Fe, it is preferably represented by the empirical formula:

$Mo_{12}Bi_pFe_qA_aB_bC_cD_dE_eO_x$ wherein A is at least one element selected from the group consisting of nickel and cobalt; B is at least one element selected from alkali metal elements; C is at least one element selected from the group consisting of magnesium, calcium, strontium, barium, zinc, and manganese; D is at least one rare earth element; E is at least one element selected from the group consisting of chromium, indium, and gallium; O is oxygen; p, q, a, b, c, d, e, and x represent an atomic ratio of bismuth, iron, A, B, C, D, E, and oxygen, respectively, to 12 molybdenum atoms; $0.1 \leq p \leq 5$, $0.5 \leq q \leq 8$, $0 \leq a \leq 10$, $0.02 \leq b \leq 2$, $0 \leq c \leq 5$, $0 \leq d \leq 5$, and $0 \leq e \leq 5$ are satisfied; and x is the number of oxygen atoms required for satisfying the valence requirement of the other elements present. As used herein the "empirical formula" represents the composition consisting of the atomic ratios of metals included in the formula and oxygen required depending on the total of the atomic ratios and the oxidation numbers. Since it is substantially impossible to specify the number of oxygen atoms in the oxide containing metals which can take various oxidation numbers, the number of oxygen is formally represented by "x". For example, when the oxide is obtained by drying and/or calcining a slurry which contains a Mo compound, a Bi compound, and a Fe compound, the atomic ratio of the metals contained in the slurry can be regarded as substantially equal to the atomic ratio of the metals in the resulting oxide. Therefore, the empirical formula of the resulting oxide is obtained by adding $O_x$ to the compositional formula of the prepared slurry. Note that, in the present specification, the formula representing the components controlled intentionally and the ratio thereof like the prepared composition of the slurry as described above is referred to as a "compositional formula". Therefore, in the case of the above-described example, the "compositional formula" is obtained by excluding $O_x$ from the empirical formula.

Although the role of the components represented by A, B, C, D, and E is not limited but in the field of the oxide catalyst using Mo, Bi, and Fe as essential components, the role is generally presumed as follows. Probably, A and E improve the activity of the catalyst; B and C stabilize the structure of the appropriate oxide containing Mo, Bi, and Fe; and D influences the reoxidation of the oxide. When p, q, a, b, c, d, and e are in preferred ranges, these effects can be expected to be much higher. In the above composition formula, as a more preferred composition, $0.1 \leq p \leq 0.5$, $1.5 \leq q \leq 3.5$, $1.7 \leq a \leq 9$, $0.02 \leq b \leq 1$, $0.5 \leq c \leq 4.5$, $0.02 \leq d \leq 0.5$, and $0 \leq e \leq 4.5$ are satisfied. As a still more preferred composition, B is rubidium, potassium or cesium; C is magnesium; and D is cerium; and $0.15 \leq p \leq 0.4$, $1.7 \leq q \leq 3$, $2 \leq a \leq 8$, $0.03 \leq b \leq 0.5$, $1 \leq c \leq 3.5$, $0.05 \leq d \leq 0.3$, and $0 \leq e \leq 3.5$ are satisfied. When A is nickel; B is rubidium, potassium or cesium; C is magnesium;

and D is cerium, there is a tendency that the yield of a conjugated diolefin is higher; its oxidative decomposition is well suppressed; and the resistance to reduction degradation can be imparted to the catalyst.

The carrier can be effectively used in an amount in the range of 30 to 70% by weight, preferably in the range of 40 to 60% by weight based on the sum total of the carrier and the oxide. The supported catalyst containing the oxide containing Mo, Bi, and Fe can be obtained by a known method, for example a method including a first step of preparing a raw material slurry, a second step of spray drying the raw material slurry, and a third step of calcining the dried product obtained in the second step. The carrier is preferably at least one selected from the group consisting of silica, alumina, titania, and zirconia, and a more suitable carrier is silica. Silica is an inert carrier compared with other carriers, and it has good affinity with metal oxides without reducing the activity and selectivity of the catalyst to an objective product. In addition, physical properties suitable for fluidized bed reaction such as particle shape, size, distribution, fluidity, and mechanical strength can be imparted to the oxide by supporting the oxide on the carrier.

(2) Production Method

The preferred embodiments of the method for producing the catalyst will be described below, the method comprising a first step of preparing a raw material slurry, a second step of spray drying the raw material slurry, and a third step of calcining the dried product obtained in the second step.

The raw material slurry is obtained by preparing a catalyst raw material in the first step, wherein element sources for each element of molybdenum, bismuth, iron, nickel, cobalt, an alkali metal element, magnesium, calcium, strontium, barium, zinc, manganese, a rare earth element, chromium, indium, and gallium include an ammonium salt, a nitrate, a hydrochloride, a sulfate, an organic acid salt, and the like, which are soluble in water or nitric acid. Particularly, an ammonium salt is preferred as a molybdenum source, and nitrate is preferred as an element source for each element of bismuth, iron, nickel, an alkaline earth, magnesium, zinc, manganese, and a rare earth element. As described above, oxides such as silica, alumina, titania, and zirconia can be used as a carrier of the oxide, wherein silica is used as a suitable carrier, and silica sol is preferred as a silica source. With respect to an impurity in silica sol, there is preferably used a silica sol containing 0.04 atoms or less of aluminum per 100 atoms of silicon, more preferably a silica sol containing 0.02 atoms or less of aluminum per 100 atoms of silicon. The raw material slurry can be prepared by adding an ammonium salt of molybdenum dissolved in water to silica sol and then adding thereto a solution of a nitrate of each element of bismuth, a rare earth element, iron, nickel, magnesium, zinc, manganese, and an alkaline earth element in water or a nitric acid solution. Thus, the raw material slurry can be prepared. In that case, the order of the addition as described above can also be changed.

In the second step, the raw material slurry obtained in the first step is spray dried to obtain spherical particles. The atomization of the raw material slurry can be performed by a method generally performed industrially such as a centrifugal system, a two fluid nozzle system, and a high pressure nozzle system. Particularly, it is desirable to perform the atomization by a centrifugal system. Next, the obtained particles are preferably dried by using air that is heated with steam, electric heater, or the like, as a drying heat source. The temperature of a drier entrance is in the range of 100 to 400° C., preferably in the range of 150 to 300° C.

In the third step, a desired catalyst is obtained by calcining the dried particles obtained in the second step. Preferably, the dried particles are optionally pre-calcined in the temperature range of 150 to 500° C., and then calcined in the temperature range of 500 to 700° C., preferably in the temperature range of 520 to 700° C. for 1 to 20 hours. The calcination can be performed using a firing furnace such as a rotary furnace, a tunnel kiln, and a muffle furnace. The particle size of the catalyst is preferably distributed in the range of 10 to 150 μm.

EXAMPLES

Hereinafter, the present invention will be described further in detail with reference to Examples; however, the present invention is not limited to Examples to be described below.

In Examples and Comparative Examples, the n-butene conversion, the 1,3-butadiene selectivity, and the yield that have been used for indicating the reaction results are defined by the following formulas:

n-butene conversion (%)=(the number of moles of n-butene reacted)/(the number of moles of n-butene supplied)·100, 1,3-butadiene selectivity (%)=(the number of moles of 1,3-butadiene produced)/(the number of moles of n-butene reacted)·100, and 1,3-butadiene yield (%)=(the number of moles of 1,3-butadiene produced)/(the number of moles of n-butene supplied)·100.

A Pyrex (registered trademark) glass fluidized bed reaction tube having an inside diameter of 25.4 mm was used as a reactor of a fluidized bed reaction system; a raw material mixed gas having a molar ratio composition of n-butene/air/helium=1/2.4-6.0/balance (n-butene concentration=12% by volume) was supplied at a flow rate of F=572-738 cc/min (in terms of NTP); and the reaction was performed at a reaction temperature of T=280-440° C., a reaction pressure of P=0.05 MPa, and a filling weight of a catalyst of W=50 g. The contact time is defined by the following formula:

Contact time (g·sec/cc)=$W/F$·60·273.15/(273.15+$T$)·($P$×1000+101.325)/101.325.

In the formula, W represents the filling amount of a catalyst (g); F represents the flow rate of a raw material mixed gas (cc/min, in terms of NTP); T represents the reaction temperature (° C.); and P represents the reaction pressure (MPa).

The analysis of the exit oxygen was conducted using gas chromatography (GC-8A (manufactured by Shimadzu), analysis column: ZY1 (manufactured by Shinwa Chemical Industries, Ltd.), carrier gas: helium, column temperature: constant at 75° C., TCD preset temperature: 80° C.) connected directly to the reactor.

The analysis of butene and 1,3-butadiene was conducted using gas chromatography (GC-2010 (manufactured by Shimadzu), analysis column: HP-ALS (manufactured by J&W), carrier gas: helium, column temperature: maintained at 100° C. for 8 minutes after gas injection, then increased to 195° C. at a rate of 10° C./minute, and then maintained at 195° C. for 40 minutes, TCD-FID (hydrogen flame ion detector) preset temperature: 250° C.) connected directly to the reactor.

Example 1

(a) Catalyst Preparation

An oxide represented by a composition of $Mo_{12}Bi_{0.60}Fe_{1.8}Ni_{5.0}K_{0.09}Rb_{0.05}Mg_{2.0}Ce_{0.75}$ was supported on 50% by weight silica to prepare a catalyst as follows. To 1835.4 g of silica sol containing 30% by weight $SiO_2$, was added a solution of 58.7 g of bismuth nitrate [$Bi(NO_3)_3·5H_2O$], 65.7 g of cerium nitrate [$Ce(NO_3)_3·6H_2O$], 146.7 g of iron nitrate [$Fe(NO_3)_3·9H_2O$], 293.4 g of nickel nitrate [$Ni(NO_3)_2·6H_2O$], 103.5 g of magnesium nitrate [$Mg(NO_3)_2·6H_2O$], 1.8 g of potassium nitrate [$KNO_3$], and 1.5 g of rubidium nitrate [$RbNO_3$] in 413.3 g of 16.6% by weight nitric acid, and thereto was finally added a solution of 427.4 g of ammonium paramolybdate [$(NH_4)6Mo_7O_{24}·4H_2O$] in 860.9 g of water. The raw material mixed liquid obtained here was sent to a parallel flow spray dryer, wherein it was dried at an inlet temperature of about 250° C. and an outlet temperature of about 140° C. The mixed liquid was atomized using an atomization apparatus provided with a dish rotator installed in the upper center of the dryer. The resulting powder was pre-calcined at 350° C. for one hour in an air atmosphere in an electric furnace and then calcined at 590° C. for two hours in an air atmosphere to obtain a catalyst.

(b) Production Reaction of 1,3-butadiene

There was charged 50 g of the catalyst obtained in the catalyst preparation step (a) into a Pyrex (registered trademark) glass fluidized bed reaction tube having an inside diameter of 25.4 mm. Thereto was supplied a raw material mixed gas having a molar ratio composition of 1-butene/air/helium=1/3.6/balance (1-butene concentration=12% by volume) at a flow rate of F=655 cc/min (in terms of NTP); and the reaction was performed at a reaction temperature of T=350° C. and a reaction pressure of P=0.05 MPa. At this time, the exit oxygen concentration=0.3% by volume, and the contact time between the catalyst and the mixed gas was 3.0 (g·sec/cc). The analysis of the gas produced in the reaction was conducted with gas chromatography directly connected to the reactor. The obtained results are shown in Table 1.

Example 2

The reaction was carried out in the same manner as in Example 1 except that the molar ratio composition of the raw material mixed gas was changed to 1-butene/air/helium=1/2.4/balance (1-butene concentration=12% by volume); the flow rate was changed to F=712 cc/min (in terms of NTP); and the reaction temperature was changed to T=300° C. At this time, the exit oxygen concentration was 0.6% by volume, and the contact time between the catalyst and the mixed gas was 3.0 (g·sec/cc). The obtained results are shown in Table 1.

Example 3

The reaction was carried out in the same manner as in Example 1 except that the molar ratio composition of the raw material mixed gas was changed to 1-butene/air/helium=1/4.4/balance (1-butene concentration=12% by volume); the flow rate was changed to F=589 cc/min (in terms of NTP); and the reaction temperature was changed to T=420° C. At this time, the exit oxygen concentration was 0.1% by volume, and the contact time between the catalyst and the mixed gas was 3.0 (g·sec/cc). The obtained results are shown in Table 1.

Example 4

The reaction was carried out in the same manner as in Example 1 except that the molar ratio composition of the raw material mixed gas was changed to 2-butene/air/helium=1/4.3/balance (2-butene concentration=12% by volume); the flow rate was changed to F=634 cc/min (in terms of NTP); and the reaction temperature was changed to T=370° C. At this time, the exit oxygen concentration was 0.6% by volume, and the contact time between the catalyst and the mixed gas was 3.0 (g·sec/cc). The obtained results are shown in Table 1.

Comparative Example 1

The reaction was carried out in the same manner as in Example 1 except that the molar ratio composition of the raw material mixed gas was changed to 1-butene/air/helium=1/3.0/balance (1-butene concentration=12% by volume); the flow rate was changed to F=589 cc/min (in terms of NTP); and the reaction temperature was changed to T=420° C. At this time, the exit oxygen concentration was 0% by volume, and the contact time between the catalyst and the mixed gas was 3.0 (g·sec/cc). The obtained results are shown in Table 1.

Comparative Example 2

The reaction was carried out in the same manner as in Example 1 except that the molar ratio composition of the raw material mixed gas was changed to 1-butene/air/helium=1/2.4/balance (1-butene concentration=12% by volume); the flow rate was changed to F=738 cc/min (in terms of NTP); and the reaction temperature was changed to T=280° C. At this time, the exit oxygen concentration was 1.4% by volume, and the contact time between the catalyst and the mixed gas was 3.0 (g·sec/cc). The obtained results are shown in Table 1.

Comparative Example 3

The reaction was carried out in the same manner as in Example 1 except that the molar ratio composition of the raw material mixed gas was changed to 1-butene/air/helium=1/4.8/balance (1-butene concentration=12% by volume); the flow rate was changed to F=572 cc/min (in terms of NTP); and the reaction temperature was changed to T=440° C. At this time, the exit oxygen concentration was 2.0% by volume, and the contact time between the catalyst and the mixed gas was 3.0 (g·sec/cc). The obtained results are shown in Table 1.

Comparative Example 4

The reaction was carried out in the same manner as in Example 1 except that the molar ratio composition of the raw material mixed gas was changed to 1-butene/air/helium=1/6.0/balance (1-butene concentration=12% by volume); the flow rate was changed to F=712 cc/min (in terms of NTP); and the reaction temperature was changed to T=300° C. At this time, the exit oxygen concentration was 3.8% by volume, and the contact time between the catalyst and the mixed gas was 3.0 (g·sec/cc). The obtained results are shown in Table 1.

Comparative Example 5

The reaction was carried out in the same manner as in Example 1 except that the molar ratio composition of the raw material mixed gas was changed to 2-butene/air/helium=1/4.8/balance (2-butene concentration=12% by volume); the flow rate was changed to F=572 cc/min (in terms of NTP); and the reaction temperature was changed to T=440° C. At this time, the exit oxygen concentration was 2.0% by volume, and the contact time between the catalyst and the mixed gas was 3.0 (g·sec/cc). The obtained results are shown in Table 1.

Comparative Example 6

The reaction was carried out in the same manner as in Example 1 except that the molar ratio composition of the raw material mixed gas was changed to 2-butene/air/helium=1/4.6/balance (2-butene concentration=12% by volume); the flow rate was changed to F=738 cc/min (in terms of NTP); and the reaction temperature was changed to T=280° C. At this time, the exit oxygen concentration was 1.7% by volume, and the contact time between the catalyst and the mixed gas was 3.0 (g·sec/cc). The obtained results are shown in Table 1.

Comparative Example 7

(a) Catalyst Preparation

An oxide represented by a composition of $Mo_{12}Bi_{1.0}K_{0.1}Mg_{8.0}Cr_{3.0}$ was supported on 50% by weight silica to prepare a catalyst as follows. To 1848.4 g of silica sol containing 30% by weight $SiO_2$, was added a solution of 97.9 g of bismuth nitrate, 242.2 g of chromium nitrate $[Cr(NO_3)_3 \cdot 9H_2O]$, magnesium nitrate, and 2.0 g of potassium nitrate in 450.7 g of 16.6% by weight nitric acid, and thereto was finally added a solution of 427.4 g of ammonium paramolybdate in 860.9 g of water. The raw material mixed liquid obtained here was sent to a parallel flow spray dryer, wherein it was dried at an inlet temperature of about 250° C. and an outlet temperature of about 140° C. The mixed liquid was atomized using an atomization apparatus provided with a dish rotator installed in the upper center of the dryer. The resulting powder was pre-calcined at 350° C. for one hour in an air atmosphere in an electric furnace and then calcined at 590° C. for two hours in an air atmosphere to obtain a catalyst.

(b) Production Reaction of 1,3-butadiene

The reaction was carried out in the same manner as in Example 1 except that 50 g of the catalyst obtained in the catalyst preparation step (a) in Comparative Example 7 were used; the molar ratio composition of the raw material mixed gas was changed to 1-butene/air/helium=1/3.2/balance (1-butene concentration=12% by volume); and the flow rate was changed to F=655 cc/min (in terms of NTP). At this time, the exit oxygen concentration was 0.2% by volume, and the contact time between the catalyst and the mixed gas was 3.0 (g·sec/cc). The obtained results are shown in Table 1.

Comparative Example 8

(a) Catalyst Preparation

An oxide represented by a composition of $Mo_{12}Fe_3Ni_6K_{0.12}Rb_{0.1}Mg_{2.9}Ce_{0.05}$ was supported on 50% by weight silica to prepare a catalyst as follows. To 1734.2 g of silica sol containing 30% by weight $SiO_2$, was added a solution of 244.4 g of iron nitrate, 4.4 g of cerium nitrate, 3.0 g of rubidium nitrate, 150 g of magnesium nitrate, and 2.4 g of potassium nitrate in 413 g of 16.6% by weight nitric acid, and thereto was finally added a solution of 427.4 g of ammonium paramolybdate in 860.9 g of water. The raw material mixed liquid obtained here was sent to a parallel flow spray dryer, wherein it was dried at an inlet temperature of about 250° C. and an outlet temperature of about 140° C. The mixed liquid was atomized using an atomization apparatus provided with a dish rotator installed in the upper center of the dryer. The resulting powder was pre-calcined at 350° C. for one hour in an air atmosphere in an electric furnace and then calcined at 590° C. for two hours in an air atmosphere to obtain a catalyst.

(b) Production Reaction of 1,3-butadiene

The reaction was carried out by repeating Comparative Example 7 using 50 g of the catalyst obtained in the catalyst preparation step (a) in Comparative Example 8. At this time, the exit oxygen concentration was 1.2% by volume, and the contact time between the catalyst and the mixed gas was 3.0 (g·sec/cc). The obtained results are shown in Table 1.

Example 5

(a) Catalyst Preparation

An oxide represented by a composition of $Mo_{12}Bi_{0.45}Fe_{1.8}Ni_{2.0}Co_{30}K_{0.09}Rb_{0.05}Mg_{2.0}Ce_{0.90}$ was supported on 50% by weight silica to prepare a catalyst as follows. To 1845.5 g of silica sol containing 30% by weight $SiO_2$, was added a solution of 44.0 g of bismuth nitrate, 78.8 g of cerium nitrate, 146.7 g of iron nitrate, 117.4 g of nickel nitrate, 176.1 g of cobalt nitrate [$Co(NO_3)_2 \cdot 6H_2O$], 103.5 g of magnesium nitrate, 1.8 g of potassium nitrate, and 1.5 g of rubidium nitrate in 382.8 g of 16.6% by weight nitric acid, and thereto was finally added a solution of 427.4 g of ammonium paramolybdate in 860.9 g of water. The raw material mixed liquid obtained here was sent to a parallel flow spray dryer, wherein it was dried at an inlet temperature of about 250° C. and an outlet temperature of about 140° C. The mixed liquid was atomized using an atomization apparatus provided with a dish rotator installed in the upper center of the dryer. The resulting powder was pre-calcined at 350° C. for one hour in an air atmosphere in an electric furnace and then calcined at 580° C. for two hours in an air atmosphere to obtain a catalyst.

(b) Production Reaction of 1,3-butadiene

The reaction was carried out by repeating Example 1 except that 50 g of the catalyst obtained in the catalyst preparation step (a) in Example 5 were used; and the molar ratio composition of the raw material mixed gas was changed to 1-butene/air/helium=1/3.8/balance (1-butene concentration=12% by volume). At this time, the exit oxygen concentration was 0.3% by volume, and the contact time between the catalyst and the mixed gas was 3.0 (g·sec/cc). The obtained results are shown in Table 1.

Example 6

(a) Catalyst Preparation

An oxide represented by a composition of $Mo_{12}Bi_{0.30}Fe_{1.2}Ni_{6.2}K_{0.20}Mg_{2.5}Ce_{0.30}Cr_{0.20}In_{0.2}$ was supported on 50% by weight silica to prepare a catalyst as follows. To 1773.7 g of silica sol containing 30% by weight of $SiO_2$, was added a solution of 29.4 g of bismuth nitrate, 26.3 g of cerium nitrate, 97.8 g of iron nitrate, 363.8 g of nickel nitrate, 16.1 g of chromium nitrate, 14.3 g of indium nitrate [$In(NO_3)_3 \cdot 3H_2O$], 129.3 g of magnesium nitrate, and 4.1 g of potassium nitrate in 386.7 g of 16.6% by weight nitric acid, and thereto was finally added a solution of 427.4 g of ammonium paramolybdate in 860.9 g of water. The raw material mixed liquid obtained here was sent to a parallel flow spray dryer, wherein it was dried at an inlet temperature of about 250° C. and an outlet temperature of about 140° C. The mixed liquid was atomized using an atomization apparatus provided with a dish rotator installed in the upper center of the dryer. The resulting powder was pre-calcined at 350° C. for one hour in an air atmosphere in an electric furnace and then calcined at 560° C. for two hours in an air atmosphere to obtain a catalyst.

(b) Production Reaction of 1,3-butadiene

The reaction was carried out by repeating Example 1 except that 50 g of the catalyst obtained in the catalyst preparation step (a) in Example 6 were used; and the molar ratio composition of the raw material mixed gas was changed to 1-butene/air/helium=1/3.3/balance (1-butene concentration=12% by volume). At this time, the exit oxygen concentration was 0.3% by volume, and the contact time between the catalyst and the mixed gas was 3.0 (g·sec/cc). The obtained results are shown in Table 1.

Example 7

(a) Catalyst Preparation

An oxide represented by a composition of $Mo_{12}Bi_{0.60}Fe_{10}Ni_{5.0}K_{0.09}Rb_{0.05}Mg_{2.0}Ce_{0.75}$ was supported on 50% by weight silica to prepare a catalyst as follows. The catalyst was obtained by repeating the catalyst preparation in Example 1 except that there were used 2275.8 g of silica sol containing 30% by weight $SiO_2$, 616.4 g of 16.6% by weight nitric acid, and 814.8 g of iron nitrate.

(b) Production Reaction of 1,3-butadiene

The reaction was carried out by repeating Example 1 except that 50 g of the oxide catalyst obtained in the catalyst preparation step (a) in Example 7 were used; the molar ratio composition of the mixed gas was changed to 1-butene/air/helium=1/3.4/balance (1-butene concentration=12% by volume); the flow rate was changed to F=644 cc/min (in terms of NTP); and the reaction temperature was changed to T=360° C. At this time, the exit oxygen concentration was 0.3% by volume, and the contact time between the catalyst and the mixed gas was 3.0 (g·sec/cc). The obtained results are shown in Table 1.

Example 8

(a) Catalyst Preparation

An oxide represented by a composition of $Mo_{12}Bi_{6.0}Fe_{1.8}Ni_{5.0}K_{0.09}Rb_{0.05}Mg_{2.0}Ce_{0.75}$ was supported on 50% by weight silica to prepare a catalyst as follows. The catalyst was obtained by repeating the catalyst preparation in Example 1 except that there were used 2681.6 g of silica sol containing 30% by weight $SiO_2$, 567.7 g of 16.6% by weight nitric acid, and 587.2 g of bismuth nitrate.

(b) Production Reaction of 1,3-butadiene

The reaction was carried out by repeating Example 7 except that 50 g of the catalyst obtained in the catalyst preparation step (a) in Example 8 were used; and the molar ratio composition of the raw material mixed gas was changed to 1-butene/air/helium=1/3.2/balance (1-butene concentration=12% by volume). At this time, the exit oxygen concentration was 0.2% by volume, and the contact time between the catalyst and the mixed gas was 3.0 (g·sec/cc). The obtained results are shown in Table 1.

Example 9

The reaction in Example 1 was continued for 450 hours to evaluate the performance of the catalyst. The performance was very stable throughout the evaluation, and after the lapse of 450 hours, the 1-butene conversion was 98.1%; the 1,3-butadiene selectivity was 93.5%; the 1,3-butadiene yield was 91.7%; and the exit oxygen concentration was 0.2% by volume, which were substantially the same results as obtained in Example 1.

Comparative Example 9

The reaction in Comparative Example 1 was continued for 450 hours to evaluate the performance of the catalyst. The performance changed with time, and after the lapse of 450 hours, the 1-butene conversion was 10.3%; the 1,3-butadiene selectivity was 6.7%; the 1,3-butadiene yield was 0.7%; and the exit oxygen concentration was 0% by volume.

Comparative Example 10

The reaction in Comparative Example 4 was continued for 450 hours to evaluate the catalyst life. The performance changed with time, and after the lapse of 450 hours, the 1-butene conversion was 86.3%; the 1,3-butadiene selectivity was 82.2%; the 1,3-butadiene yield was 70.9%; and the exit oxygen concentration was 3.3% by volume.

Comparative Example 11

The reaction in Comparative Example 7 was continued for 450 hours to evaluate the catalyst life. The performance changed with time, and after the lapse of 450 hours, the 1-butene conversion was 63.7%; the 1,3-butadiene selectivity was 66.7%; the 1,3-butadiene yield was 42.5%; and the exit oxygen concentration was 1.8% by volume.

of 1,3-butadiene and isoprene, thereby allowing high-yield and stable production of 1,3-butadiene and isoprene over a long period of time.

The invention claimed is:

1. A method for production of a conjugated diolefin comprising bringing a catalyst in which an oxide is supported on a carrier into contact with a monoolefin having four carbon atoms in a fluidized bed reactor in which the catalyst and oxygen are present, wherein the method satisfies the following (1) to (3):
   (1) the oxide contains Mo, Bi, and Fe;
   (2) a reaction temperature is in a range of 300 to 420° C.; and
   (3) an oxygen concentration in a reactor outlet gas is in a range of 0.05 to 0.7% by volume;
   wherein the oxide is represented by the following empirical formula:

$$Mo_{12}Bi_pFe_gA_aB_bC_cD_dE_eO_x$$

TABLE 1

| Catalyst | | Temperature (° C.) | Exit oxygen concentration (vol %) | Butene species | Butene conversion (%) | 1,3-Butadiene selectivity (%) | 1,3-Butadiene yield (%) |
|---|---|---|---|---|---|---|---|
| Example 1 | $Mo_{12}Bi_{0.60}Fe_{1.8}Ni_{5.0}K_{0.09}Rb_{0.05}Mg_{2.0}Ce_{0.75}O_x$/50 wt % $SiO_2$ | 350 | 0.3 | 1-butene | 97.2 | 94.5 | 91.9 |
| Example 2 | $Mo_{12}Bi_{0.60}Fe_{1.8}Ni_{5.0}K_{0.09}Rb_{0.05}Mg_{2.0}Ce_{0.75}O_x$/50 wt % $SiO_2$ | 300 | 0.6 | 1-butene | 91.2 | 95.6 | 87.2 |
| Example 3 | $Mo_{12}Bi_{0.60}Fe_{1.8}Ni_{5.0}K_{0.09}Rb_{0.05}Mg_{2.0}Ce_{0.75}O_x$/50 wt % $SiO_2$ | 420 | 0.1 | 1-butene | 98.8 | 84.0 | 83.0 |
| Example 4 | $Mo_{12}Bi_{0.60}Fe_{1.8}Ni_{5.0}K_{0.09}Rb_{0.05}Mg_{2.0}Ce_{0.75}O_x$/50 wt % $SiO_2$ | 370 | 0.6 | 2-butene | 98.0 | 89.8 | 88.0 |
| Comparative Example 1 | $Mo_{12}Bi_{0.60}Fe_{1.8}Ni_{5.0}K_{0.09}Rb_{0.05}Mg_{2.0}Ce_{0.75}O_x$/50 wt % $SiO_2$ | 420 | 0.0 | 1-butene | 99.8 | 69.4 | 69.3 |
| Comparative Example 2 | $Mo_{12}Bi_{0.60}Fe_{1.8}Ni_{5.0}K_{0.09}Rb_{0.05}Mg_{2.0}Ce_{0.75}O_x$/50 wt % $SiO_2$ | 280 | 1.4 | 1-butene | 75.4 | 93.9 | 70.8 |
| Comparative Example 3 | $Mo_{12}Bi_{0.60}Fe_{1.8}Ni_{5.0}K_{0.09}Rb_{0.05}Mg_{2.0}Ce_{0.75}O_x$/50 wt % $SiO_2$ | 440 | 2.0 | 1-butene | 99.8 | 62.2 | 62.1 |
| Comparative Example 4 | $Mo_{12}Bi_{0.60}Fe_{1.8}Ni_{5.0}K_{0.09}Rb_{0.05}Mg_{2.0}Ce_{0.75}O_x$/50 wt % $SiO_2$ | 300 | 3.8 | 1-butene | 83.4 | 87.2 | 72.7 |
| Comparative Example 5 | $Mo_{12}Bi_{0.60}Fe_{1.8}Ni_{5.0}K_{0.09}Rb_{0.05}Mg_{2.0}Ce_{0.75}O_x$/50 wt % $SiO_2$ | 440 | 2.0 | 2-butene | 99.5 | 62.6 | 62.3 |
| Comparative Example 6 | $Mo_{12}Bi_{0.60}Fe_{1.8}Ni_{5.0}K_{0.09}Rb_{0.05}Mg_{2.0}Ce_{0.75}O_x$/50 wt % $SiO_2$ | 280 | 1.7 | 2-butene | 70.1 | 93.0 | 65.2 |
| Comparative Example 7 | $Mo_{12}Bi_{1.0}K_{0.1}Mg_{8.0}Cr_{3.0}O_x$/50 wt % $SiO_2$ | 350 | 0.5 | 1-butene | 78.4 | 79.2 | 62.1 |
| Comparative Example 8 | $Mo_{12}Fe_{3.0}Ni_{6.0}K_{0.12}Rb_{0.10}Mg_{2.9}Ce_{0.05}O_x$/50 wt % $SiO_2$ | 350 | 1.2 | 1-butene | 67.8 | 75.6 | 51.2 |
| Example 5 | $Mo_{12}Bi_{0.45}Fe_{1.8}Ni_{2.0}Co_{3.0}K_{0.09}Rb_{0.05}Mg_{2.0}Ce_{0.90}O_x$/50 wt % $SiO_2$ | 350 | 0.3 | 1-butene | 97.7 | 93.5 | 91.3 |
| Example 6 | $Mo_{12}Bi_{0.30}Fe_{1.2}Ni_{6.2}K_{0.20}Mg_{2.5}Ce_{0.30}Cr_{0.20}In_{0.2}O_x$/50 wt % $SiO_2$ | 350 | 0.3 | 1-butene | 98.0 | 93.2 | 91.3 |
| Example 7 | $Mo_{12}Bi_{0.60}Fe_{10}Ni_{5.0}K_{0.09}Rb_{0.05}Mg_{2.0}Ce_{0.75}O_x$/50 wt % $SiO_2$ | 360 | 0.3 | 1-butene | 87.6 | 90.2 | 79.0 |
| Example 8 | $Mo_{12}Bi_{6.0}Fe_{1.8}Ni_{5.0}K_{0.09}Rb_{0.05}Mg_{2.0}Ce_{0.75}O_x$/50 wt % $SiO_2$ | 360 | 0.2 | 1-butene | 84.4 | 93.1 | 78.6 |

As apparent from the results in Table 1, 1,3-butadiene can be produced in high yield even in a fluidized bed reaction system when 1,3-butadiene is produced by the oxidative dehydrogenation of n-butene by using an oxide containing Mo, Bi, and Fe which is supported on a carrier as the catalyst in the present embodiment and setting the exit oxygen concentration and the reaction temperature of a fluidized bed reactor in specific ranges.

INDUSTRIAL APPLICABILITY

When monoolefins having four or more carbon atoms such as n-butene and isopentene and molecular oxygen are subjected to catalytic oxidative dehydrogenation to produce conjugated diolefins corresponding to these monoolefins such as 1,3-butadiene and isoprene, respectively, the production method by the fluidized bed reaction system of the present invention can suitably suppress the oxidative decomposition wherein A is at least one element selected from the group consisting of nickel and cobalt; B is at least one element selected from alkali metal elements; C is at least one element selected from the group consisting of magnesium, calcium, strontium, barium, zinc, and manganese; D is at least one rare earth element; E is at least one element selected from the group consisting of chromium, indium, and gallium; O is oxygen; p, q, a, b, c, d, e, and x represent an atomic ratio of bismuth, iron, A, B, C, D, E, and oxygen, respectively, to 12 molybdenum atoms; $0.1 \leq p \leq 5$, $0.5 \leq q \leq 8$, $1.7 \leq a \leq 10$, $0.02 \leq b \leq 2$, $0.5 \leq c \leq 5$, $0.02 \leq d \leq 5$, and $0 \leq e \leq 5$ are satisfied; and x is the number of oxygen atoms required for satisfying the valence requirement of the other elements present.

2. The method for production of the conjugated diolefin according to claim 1, wherein the carrier is at least one selected from the group consisting of silica, alumina, titania, and zirconia.

3. The method for production of the conjugated diolefin according to claim 1, wherein an atomic ratio of Bi of p and an atomic ratio of Fe of q to an atomic ratio of Mo of 12 in the oxide satisfy $0.1 \leq p \leq 5$ and $0.5 \leq q \leq 8$.

4. The method for production of the conjugated diolefin according to claim 1, wherein the monoolefin having four carbon atoms is n-butene.

5. The method for production of the conjugated diolefin according to claim 2, wherein an atomic ratio of Bi of p and an atomic ratio of Fe of q to an atomic ratio of Mo of 12 in the oxide satisfy $0.1 \leq p \leq 5$ and $0.5 \leq q \leq 8$.

6. The method for production of the conjugated diolefin according to claim 2, wherein the monoolefin having four carbon atoms is n-butene.

7. The method for production of the conjugated diolefin according to claim 3, wherein the monoolefin having four carbon atoms is n-butene.

8. The method for production of the conjugated diolefin according to claim 5, wherein the monoolefin having four carbon atoms is n-butene.

* * * * *

UNITED STATES PATENT AND TRADEMARK OFFICE
CERTIFICATE OF CORRECTION

PATENT NO. : 8,546,634 B2
APPLICATION NO. : 12/893339
DATED : October 1, 2013
INVENTOR(S) : Hideo Midorikawa et al.

Page 1 of 1

It is certified that error appears in the above-identified patent and that said Letters Patent is hereby corrected as shown below:

In the Claims

In claim 1, column 16, line 20, "$Mo_{12}Bi_pFe_gA_aB_bC_cD_dE_eO_x$" should read --$Mo_{12}Bi_pFe_qA_aB_bC_cD_dE_eO_x$--.

Signed and Sealed this
Fourth Day of March, 2014

Michelle K. Lee
*Deputy Director of the United States Patent and Trademark Office*